United States Patent [19]
Allard et al.

[11] Patent Number: 5,928,629
[45] Date of Patent: Jul. 27, 1999

[54] PHOTOPROTECTIVE/COSMETIC COMPOSITIONS COMPRISING DIBENZOYLMETHANE/TRIAZINE/DIPHENYLACRYLATE COMPOUNDS

[75] Inventors: Delphine Allard, Colombes; Serge Forestier, Claye Souilly, both of France

[73] Assignee: Société L'Oréal S.A., Paris, France

[21] Appl. No.: 08/886,245

[22] Filed: Jul. 1, 1997

[30] Foreign Application Priority Data

Jul. 1, 1996 [FR] France .................................. 96 08172

[51] Int. Cl.$^6$ ............................ A61K 7/42; A61K 31/53; A61K 31/12; A61K 7/00
[52] U.S. Cl. ............................... 424/59; 424/60; 424/400; 424/401; 514/241; 514/679
[58] Field of Search .................. 424/59, 60, 400, 424/401; 514/241, 679

[56] References Cited

FOREIGN PATENT DOCUMENTS

| | | |
|---|---|---|
| 0685221 | 12/1995 | European Pat. Off. . |
| 0689828 | 1/1996 | European Pat. Off. . |

*Primary Examiner*—Shelley A. Dodson
*Attorney, Agent, or Firm*—Burns, Doane, Swecker & Mathis, L.L.P.

[57] ABSTRACT

Improvedly photostable, topically applicable cosmetic/dermatological sunscreen compositions well suited for enhanced photoprotection of human skin and/or hair against the damaging effects of UV-A and UV-B irradiation, particularly solar radiation, comprise (i) 4-tert-butyl-4'-methoxydibenzoylmethane, (ii) at least one particular 1,3,5-triazine compound, and (iii) at least one alkyl β,β'-diphenylacrylate or alkyl α-cyano-β,β'-diphenylacrylate, formulated in a cosmetically/dermatologically acceptable vehicle, diluent or carrier therefor.

21 Claims, No Drawings

PHOTOPROTECTIVE/COSMETIC COMPOSITIONS COMPRISING DIBENZOYLMETHANE/TRIAZINE/DIPHENYLACRYLATE COMPOUNDS

BACKGROUND OF THE INVENTION

1. Technical Field of the Invention

The present invention relates to novel cosmetic and/or dermatological compositions (hereinafter sometimes "anti-sun" or "sunscreen" compositions) for the photoprotection of the skin and/or the hair against UV radiation, in particular solar radiation. More especially, this invention relates to novel cosmetic and/or dermatological compositions exhibiting improved photostability and including, in a cosmetically and/or dermatologically acceptable substrate (vehicle, diluent or carrier), the combination of three specific screening agents.

The present invention also relates to the use of the subject compositions in the cosmetic and/or dermatological fields.

2. Description of the Prior Art

It is known to this art that light radiation of wavelengths of from 280 nm to 400 nm permits the human epidermis to tan and that irradiation of wavelengths of from 280 nm to 320 nm, i.e., UV-B irradiation, causes erythemas and skin burns which can be harmful to the development of the natural tan; hence, this UV-B radiation must therefore be screened from the skin.

It is also known to this art that UV-A radiation, of wavelengths of from 320 nm to 400 nm, which promotes tanning of the skin, also adversely affects it, especially in the case of a sensitive skin or of a skin which is continually exposed to solar radiation. UV-A rays cause, in particular, a loss in the elasticity of the skin and the appearance of wrinkles, promoting a premature aging thereof. Such irradiation promotes triggering of the erythematous reaction or amplifies this reaction in certain individuals and may even be the source of phototoxic or photoallergic reactions. It is therefore desirable to also filter or screen out the UV-A radiation.

Thus, for purposes of ensuring protection of the skin and of the hair against all of the UV radiation which is as complete as possible and as efficacious as possible, combinations of screening agents which are active in the UV-A region and of screening agents which are active in the UV-B region are typically employed in the formulation of sunscreen compositions.

In this respect, 4-tert-butyl-4'-methoxydibenzoylmethane, marketed under the trademark "Parsol 1789" by Givaudan is a particularly advantageous screening agent active in the UV-A region, taking account of its high intrinsic absorptivity.

Similarly, 1,3,5-triazine derivatives and in particular, 2,4,6-tris[p-(2'-ethylhexyl-1'-oxycarbonyl) anilino]-1,3,5-triazine, marketed under the trademark "Uvinul T 150" by BASF, have a high absorptivity for UV-B radiation. Therefore, it would be very advantageous to employ same in combination with the aforementioned 4-tert-butyl-4'-methoxydibenzoylmethane with a view towards providing products offering wide and efficacious protection throughout the entire range of UV radiation.

However, it has now been demonstrated that in the presence of 4-tert-butyl-4'-methoxydibenzoylmethane and under UV irradiation, the aforesaid 1,3,5-triazine derivatives present the disadvantage of being extensively degraded chemically. Under these conditions, the combination of the two screening agents no longer provides a prolonged broad protection of the skin and of the hair against solar radiation.

SUMMARY OF THE INVENTION

It has now unexpectedly been determined that the formulation of an alkyl β,β'-diphenylacrylate or alkyl α-cyano-β,β'-diphenylacrylate into compositions containing 4-tert-butyl-4'-methoxydibenzoylmethane in combination with at least one 1,3,5-triazine derivative, and in particular with 2,4,6-tris[p-(2'-ethylhexyl-1'-oxycarbonyl) anilino]-1,3,5-triazine, markedly enhances the stability of such at least one 1,3,5-triazine derivative within such compositions, and hence markedly enhances the overall effectiveness of these compositions.

Briefly, the present invention features novel cosmetic and/or dermatological compositions comprising, in a cosmetically and/or dermatologically acceptable carrier, diluent or vehicle, (i) 4-tert-butyl-4'-methoxydibenzoylmethane, (ii) at least one 1,3,5-triazine compound having the following structural formula (I):

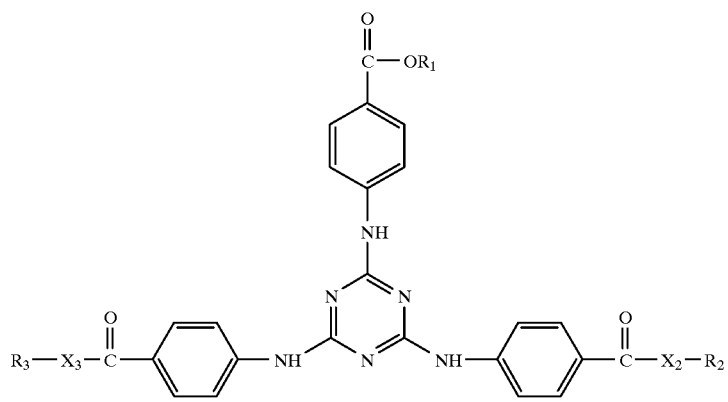

wherein $X_2$ and $X_3$, which may be identical or different, are each an oxygen atom or the -NH- radical; and $R_1$, $R_2$ and $R_3$, which may be identical or different, are each a hydrogen atom, an alkali metal, an ammonium radical optionally substituted by one or more alkyl or hydroxyalkyl radicals, a linear or branched $C_1$-$C_{18}$ alkyl radical, a $C_5$-$C_{12}$ cycloalkyl radical optionally substituted by one or more $C_1$-$C_4$ alkyl radicals, a polyoxyethylenated radical having from 1 to 6 ethylene oxide units and in which the terminal OH group is methylated, or a radical of the following formulae (II), (III) and (IV):

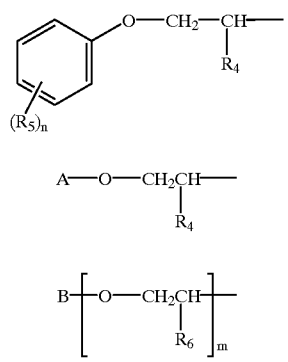

wherein $R_4$ is hydrogen or a methyl radical, $R_5$ is a $C_1$-$C_9$ alkyl radical, n is an integer ranging from 0 to 3, m is an integer ranging from 1 to 10, A is a $C_4$-$C_8$ alkyl radical or a $C_5$-$C_8$ cycloalkyl radical, B is a linear or branched $C_1$-$C_8$ alkyl radical, a $C_5$-$C_8$. cycloalkyl radical, or an aryl radical optionally substituted by one or more $C_1$-$C_4$ alkyl radicals, and $R_6$ is hydrogen or a methyl radical, and (iii) at least one alkyl β,β'-diphenylacrylate or alkyl α-cyano-β,β'-diphenylacrylate having the following structural formula (V):

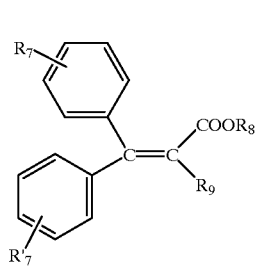

in which $R_7$ and $R'_7$, which may be identical or different, are in a meta- or para- position and are each a hydrogen atom, a straight or branched chain $C_1$-$C_8$ alkoxy radical, or a straight or branched chain $C_1$-$C_4$ alkyl radical; R8 is a straight or branched chain $C_1$-$C_{12}$ alkyl radical; and $R_9$ is a hydrogen atom or a -CN radical, with the proviso that said compositions are devoid of 2-ethylhexyl p-methoxycinnamate.

DETAILED DESCRIPTION OF BEST MODE AND SPECIFIC/PREFERRED EMBODIMENTS OF THE INVENTION

More particularly according to the present invention, cosmetic and/or dermatological compositions containing 4-tert-butyl-4'-methoxydibenzoylmethane in combination with at least one 1,3,5-triazine derivative are provided, in which compositions the concentration of 1,3,5-triazine compound remains relatively constant even if the compositions are subjected to the action of light.

Further, the alkyl β,β'-diphenylacrylates or alkyl α-cyano-β,β'-diphenylacrylates of the present invention present the advantage of possessing a good intrinsic screening power which contributes to the protection against UV irradiation conferred by the subject compositions and, in addition, the complete screening system [4-tert-butyl-4'-methoxydibenzoylmethane +1,3,5-triazine derivative +(alkyl β,β'-diphenylacrylate or α-cyano-β,β'-diphenylacrylate)] exhibits overall a very good stability under the action of UV (photostability), which presents another advantage of the compositions according to the invention.

The present invention also features the use of an alkyl β,β'-diphenylacrylate or alkyl α-cyano-β,β'-diphenylacrylate in, or for the formulation of, cosmetic and/or dermatological compositions containing 4-tert-butyl-4'-methoxydibenzoylmethane in combination with at least one 1,3,5-triazine compound as described above with a view to improving the stability to UV radiation (photostability) of said at least one 1,3,5-triazine compound in the subject compositions.

This invention also features a process for improving the stability to UV radiation (photostability) and, hence, the effectiveness of a cosmetic and/or dermatological composition comprising 4-tert-butyl-4'-methoxydibenzoylmethane and a 1,3,5-triazine compound as described above, in particular 2,4,6-tris[p-(2'-ethylhexyl-1'-oxycarbonyl)anilino]-1,3,5-triazine, said process entailing incorporating into said composition an effective photostabilizing amount of an alkyl β,β'-diphenylacrylate or alkyl α-cyano-β,β'-diphenylacrylate.

A first compound of the compositions according to the invention is, therefore, 4-tert-butyl-4'-methoxydibenzoylmethane. This compound is a screening agent which is per se well known and which has a high absorptivity in the UV-A region with a maximum at 358 nm. It is commercially available under the trademark of "Parsol 1789" by Givaudan and has the following structural formula (VI):

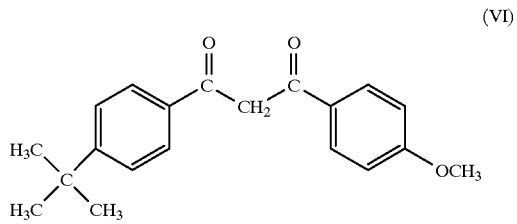

4-Tert-butyl-4'-methoxydibenzoylmethane is advantageously present in the compositions of the invention in an amount ranging from 0.2% to 15% by weight, relative to the total weight of the composition. This amount preferably ranges from 0.5% to 10%.

The second compound of the compositions of the present invention is a specific 1,3,5-triazine compound. The 1,3,5-triazine compounds of the present invention are thus selected from among those having the following structural formula (I):

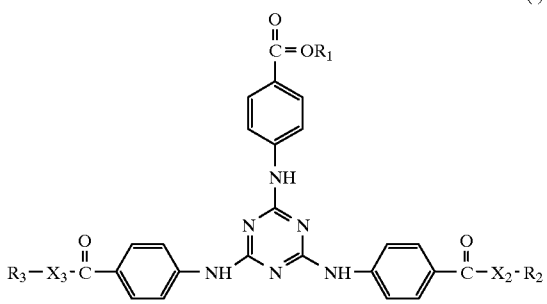

(I)

in which $X_2$ and $X_3$, which may be identical or different, are each an oxygen atom or the -NH-radical; and $R_1$, $R_2$ and $R_3$, which may be identical or different, are each a hydrogen atom, an alkali metal, an ammonium radical optionally substituted by one or more alkyl or hydroxyalkyl radicals, a linear or branched $C_1$-$C_{18}$ alkyl radical, a $C_5$-$C_{12}$ cycloalkyl radical optionally substituted by one or more $C_1$-$C_4$ alkyl radicals, a polyoxyethylenated radical including from 1 to 6 ethylene oxide units and in which the terminal OH group is methylated, or a radical of the following formulae (II), (III) and (IV):

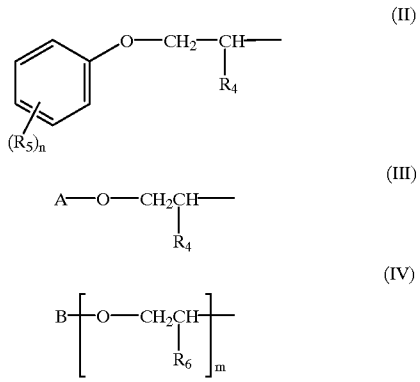

wherein $R_4$ is hydrogen or a methyl radical, R5 is a $C_1$-$C_9$ alkyl radical, n is an integer ranging from 0 to 3, m is an integer ranging from 1 to 10, A is a $C_4$-$C_8$ alkyl radical or a $C_5$-$C_8$ cycloalkyl radical, B is a linear or branched $C_1$-$C_8$ alkyl radical, a $C_5$-$C_8$ cycloalkyl radical or an aryl radical optionally substituted by one or more $C_1$-$C_4$ alkyl radicals, and $R_6$ is hydrogen or a methyl radical.

A first, more particularly preferred class of 1,3,5-triazine compounds is that especially described in EP-A-0 517 104, of the 1,3,5-triazines having the above formula (I) and exhibiting all of the following characteristics:

$X_2$ and $X_3$ are identical and are each an oxygen atom $R_1$ is a $C_5$-$C_{12}$ cycloalkyl radical optionally substituted by one or more $C_1$-$C_4$ alkyl radicals, or a radical of formula (II), (III) or (IV) above, in which:

B is a $C_1$-$C_4$ alkyl radical, $R_6$ is the methyl radical, $R_2$ and $R_3$, which may be identical or different, are each hydrogen, an alkali metal, an ammonium radical optionally substituted by one or more alkyl or hydroxyalkyl radicals, a linear or branched $C_1$-$C_{18}$ alkyl radical, a $C_5$-$C_{12}$ cycloalkyl radical optionally substituted by one or more $C_1$-$C_4$ alkyl radicals, or a radical of formula (II), (III) or (IV) above in which:

B is a $C_1$-$C_4$ alkyl radical, $R_6$ is the methyl radical.

A second preferred class of 1,3,5-triazine compounds according to the invention is that especially described in EP-A-0 570 838, of the 1,3,5-triazines having the formula (I) and exhibiting the combination of the following characteristics:

$X_3$ is the -NH- radical, $R_3$ is a linear or branched $C_1$-$C_{18}$ alkyl radical, or a $C_5$-$C_{12}$ cycloalkyl radical optionally substituted by one or more $C_1$-$C_4$ alkyl radicals, $R_1$ is hydrogen, an alkali metal, an ammonium radical, a radical of formula (IV), a linear or branched $C_1$-$C_{18}$, alkyl radical or a $C_5$-$C_{12}$ cycloalkyl radical optionally substituted by one or more $C_1$-$C_4$ alkyl radicals, with the provisos that:

if $X_2$ is the -NH- radical, then $R_2$ is a linear or branched $C_1$-$C_{18}$ alkyl radical or a $C_5$-$C_{12}$ cycloalkyl radical optionally substituted by one or more $C_1$-$C_4$ alkyl radicals, and if $X_2$ is oxygen, then $R_2$ is hydrogen, an alkali metal, an ammonium radical, a radical of formula (IV), a linear or branched $C_1$-$C_{18}$ alkyl radical or a $C_5$-$C_{12}$ cycloalkyl radical optionally substituted by one or more $C_1$-$C_4$ alkyl radicals.

A particularly preferred 1,3,5-triazine of this second class is that having the following structural formula:

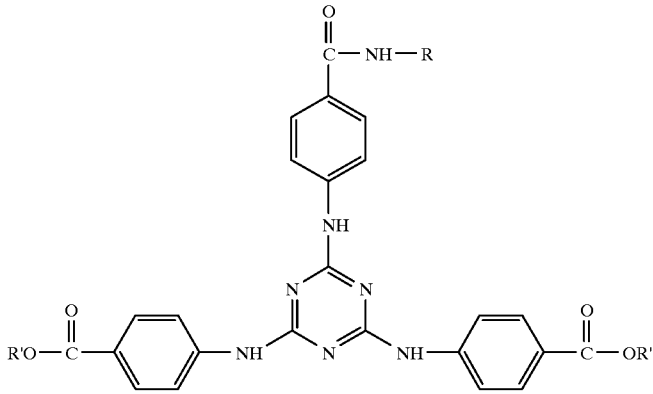

in which R'is a 2-ethylhexyl radical and R is a tert-butyl radical.

A third preferred class of compounds is that especially described in U. S. Pat. No. 4,724,137, of 1,3,5-triazines having the formula (I) and exhibiting all of the following characteristics:

$X_2$ and $X_3$ are identical and are each an oxygen atom, $R_1$, $R_2$ and $R_3$ are identical and are each a $C_6$-$C_{12}$ alkyl radical or a polyoxyethylene radical having from 1 to 6 ethylene oxide units and in which the terminal OH group is methylated.

A particularly preferred 1,3,5-triazine of this third class is 2,4,6-tris[p-(2'-ethylhexyl-1'-oxycarbonyl) anilino]-1,3,5-triazine, which is a screening agent per se known to this art, which is active in the UV-B region, which is in a solid form and which is commercially available under the trademark "Uvinul T 150" by BASF. This compound has the following structural formula:

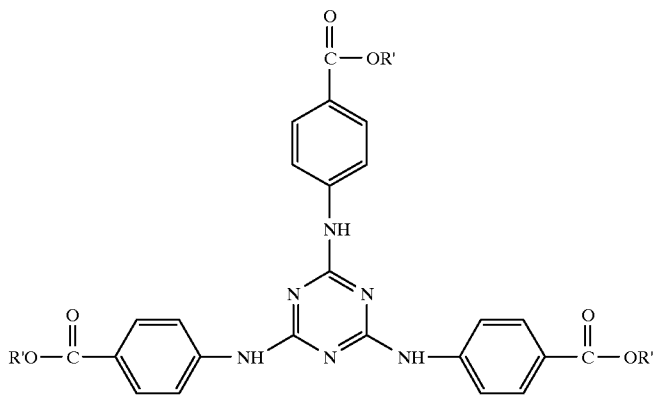

in which R' is a 2-ethylhexyl radical.

The 1,3,5-triazine derivative(s) is (are) generally present in the compositions of the invention in an amount that can range from 0.5% to 20%, preferably from 1% to 10% by weight, relative to the total weight of the composition.

A third, absolutely essential, compound of the compositions according to the invention is a compound of the class including alkyl β,β'-diphenyl-acrylates and alkyl α-cyano-β,β'-diphenylacrylates. The alkyl β,β'-diphenylacrylates and alkyl α-cyano-β,β'-diphenylacrylates according to the present invention are selected from among those having the following structural formula (V):

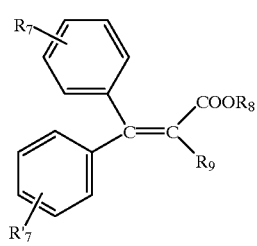

(V)

in which $R_7$ and $R'_7$, which may be identical or different, are in a meta- or para- position and are each hydrogen, a straight or branched chain $C_1$-$C_8$ alkoxy, or a straight or branched chain $C_1$-$C_4$ alkyl radical, $R_8$, is a straight or branched chain $C_1$-$C_{12}$ alkyl radical, and $R_9$ is a hydrogen atom or a -CN radical.

Among the alkyl β,β'-diphenylacrylates and alkyl α-cyano-β,β'-diphenylacrylates according to the present invention, more particularly preferred are 2-ethylhexyl α-cyano-β,β'-diphenylacrylate and ethyl α-cyano-β,β'-diphenylacrylate.

2-Ethylhexyl α-cyano-β,β'-diphenylacrylate, also designated octocrylene, is a known lipophilic screening agent absorbing in the UV-B region. It is available commercially and marketed under the trademark "Uvinul N 539" by BASF. It has the following structural formula:

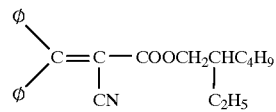

in which ø denotes a phenyl radical.

Ethyl α-cyano-β,β' diphenylacrylate, also designated etocrylene, is also a liposoluble screening agent, absorbing in the UV-B region. It is available commercially and marketed under the trademark "Uvinul N 35" by BASF. It has to the following structural formula:

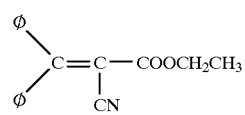

in which ø denotes a phenyl radical.

Thus, when an alkyl β,β'-diphenylacrylate or alkyl α-cyano-β,β'-diphenylacrylate is added in sufficient quantity to an antisun or sunscreen composition containing 4-tert-butyl-4'-methoxydibenzoylmethane and a 1,3,5-triazine derivative as described above, an increase in the stability of said 1,3,5-triazine derivative to light is observed and, hence, an improvement in the effectiveness of the photoprotecting composition over the course of time.

The alkyl β,β'-diphenylacrylate or alkyl α-cyano-β,β'-diphenylacrylate is preferably present in the compositions according to the invention in an amount of at least 0.5% by weight, relative to the total weight of the composition. This amount also preferably ranges from 0.5% to 20% by weight, relative to the total weight of the composition.

The cosmetic and/or dermatological compositions of the present invention may, of course, contain one or several additional sunscreens which are active in the UV-A and/or UV-B region (absorbers) which are hydrophilic or lipophilic, other, naturally, than the three screening agents indicated above. These additional screening agents are advantageously selected from among cinnamic compounds, salicylic compounds, benzylidene camphor compounds, benzimidazole compounds, triazine compounds other than those indicated above, benzophenone compounds, $\beta,\beta'$-diphenylacrylate compounds other than those indicated above, p-aminobenzoic acid compounds and the polymer screening agents and silicone screening agents described in WO-93/04665. Other examples of organic screening agents are provided in EP-A 0,487,404.

The compositions according to the invention preferably do not contain 2-ethylhexyl p-methoxycinnamate. Indeed, 2-ethylhexyl p-methoxycinnamate can destabilize compositions comprising 4-tert-butyl-4'-methoxydibenzoylmethane and a 1,3,5-triazine compound, such as the subject compositions.

The compositions of this invention may also contain agents for artificial tanning and/or darkening of the skin (self-tanning agents), such as, for example, dihydroxyacetone (DHA).

The cosmetic and/or dermatological compositions of the invention may further contain pigments or nanopigments (primary particle mean size generally ranging from 5 nm to 100 nm, preferably from 10 to 50 nm) of coated or uncoated metal oxides such as, for example, nanopigments of oxide of titanium (amorphous or crystalline in rutile and/or anatase form), of iron, of zinc, of zirconium or of cerium, which are all photoprotective agents which are per se well known to this art, acting by physical blocking (reflection and/or scattering) of UV radiation. Conventional coating agents are, furthermore, alumina and/or aluminum stearate. Such coated or uncoated metal oxide nanopigments are described, in particular, in EP-A-0,518,772 and EP-A-0,518,773.

The compositions of the present invention may additionally include conventional cosmetic additives and adjuvants selected, in particular, from among fatty substances, organic solvents, ionic or nonionic thickeners, softeners, antioxidants, agents against anti-free radical agents, opacifiers, stabilizers, emollients, silicones, α-hydroxyacids, antifoam agents, hydrating agents, vitamins, perfumes, stabilizers, surfactants, fillers, sequestrants, preservatives, polymers, propellants, alkalifying or acidifying agents, dyes and colorants or any other ingredient usually employed in the cosmetic and/or dermatological field, in particular for the production of antisun/sunscreen compositions in emulsion form.

The fatty substances may be an oil or a wax or mixtures thereof. By "oil" is intended a compound which is liquid at ambient temperature. By "wax" is intended a compound that is solid or substantially solid at ambient temperature, and whose melting point is generally higher than 35° C.

Exemplary oils include mineral oils (liquid petrolatum), vegetable oils (sweet almond, macadamia, blackcurrant pip or jojoba oil), synthetic oils such as perhydrosqualene, fatty alcohols, acids or esters (such as the benzoate of $C_{12}$-$C_{15}$ alcohols, marketed under the trademark "Finsolv TN" by Finetex, octyl palmitate, isopropyl lanolate or triglycerides including those of capric/caprylic acids), oxyethylenated or oxypropylenated fatty esters and ethers, siliconated (cyclomethicone, polydimethyl siloxanes or PDMS) or fluorinated oils and polyalkylenes.

Exemplary waxy compounds include paraffin wax, carnauba wax, beeswax and hydrogenated castor oil.

The lower alcohols and polyols are representative of the organic solvents.

And exemplary thickeners include crosslinked polyacrylic acids, guar gums and modified or unmodified celluloses such as hydroxypropylated guar gum, methyl hydroxyethyl cellulose and hydroxypropyl methyl cellulose.

One skilled in this art will, of course, take care to select the aforementioned additional optional compound(s) (in particular the additional screening agents) and/or their amounts such that the advantageous properties inherent in the ternary association in accordance with the invention are not, or are substantially not, adversely affected by the envisaged incorporation(s).

The compositions according to the invention can be prepared via techniques which are well known to this art, in particular those intended for the preparation of emulsions of oil-in-water or water-in-oil type.

The subject compositions may be formulated in the form of an emulsion, simple or complex (O/W, W/O, O/W/O or W/O/W) such as a cream, a milk, an ointment, or in the form of a gel or of a cream gel, of powder, of solid stick and optionally may be packaged as an aerosol and be in the form of a mousse or spray.

The compositions according to the invention are preferably formulated as oil-in-water emulsions.

When an emulsion, the aqueous phase thereof may include a nonionic vesicular dispersion prepared according to known techniques (Bangham, Standish and Watkins, J. Mol. Biol., 13, 238 (1965), FR-2,315,991 and FR-2,416,008).

The cosmetic and/or dermatological compositions of the invention are well suited for protecting human skin or hair against the deleterious effects of ultraviolet radiation, as antisun compositions or as makeup products.

When the cosmetic compositions of this invention are employed for the protection of human skin against UV rays or as antisun compositions, they may be formulated as suspensions or dispersions in solvents or as fatty substances, in the form of nonionic vesicular dispersions or in the form of an emulsions, preferably of the oil-in-water type, such as a cream or a milk, in the form of salve, gel, cream, ointment, gel, solid stick, stick, aerosol mousse or spray.

When the cosmetic composition according to the invention is employed for protecting the hair, they may be formulated in the form of shampoo, lotion, gel, emulsion, nonionic vesicular dispersion, hair-fixing spray and may, for example, constitute a composition to be rinsed away, to be applied before or after shampooing, before or after dyeing or bleaching, before, during or after permanent waving or straightening, a styling or treatment lotion or gel, a lotion or gel for blow-drying or hair-setting, or a composition for permanent waving or straightening, dyeing or bleaching the hair.

When the subject compositions are employed as products for making up the eyelashes, the eyebrows or the skin, such as a cream for treating the skin, a foundation, a lipstick, an eye shadow, a blusher, mascara or eyeliner, they may be in anhydrous or aqueous solid or pasty form such as oil-in-water or water-in-oil emulsions, nonionic vesicular dispersions or suspensions.

By way of example, in the case of antisun/sunscreen formulations in accordance with the invention which comprise a carrier of the oil-in-water emulsion type, the aqueous phase (including, especially, the hydrophilic screening agents) generally constitutes from 50% to 95% by weight, preferably from 70% to 90% by weight, relative to the combined formulation, the oily phase (including, especially, the lipophilic screening agents) from 5% to 50% by weight, preferably from 10% to 30% by weight, relative to the combined formulation, and the (co)emulsifier(s) constitute from 0.5% to 20% by weight, preferably from 2% to 10% by weight, relative to the combined formulation.

The present invention thus also features a cosmetic treatment regime for protecting the skin and/or the hair against UV radiation, in particular solar radiation, comprising topically applying thereto an effective photoprotecting amount of a cosmetic composition as described above.

In order to further illustrate the present invention and the advantages thereof, the following specific examples are given, it being understood that same are intended only as illustrative and in nowise limitative.

EXAMPLES

Four oil-in-water emulsions A, B, C and D were produced, in which the common carrier had the following composition (the quantities are expressed in % of weight relative to the total weight of the composition):

| | | |
|---|---|---|
| (a) 80/20 mixture of cetylstearyl alcohol and of oxyethylenated cetylstearyl alcohol (33 EO) marketed under the trademark "Dehsconet 390" by Tensia | | 7 % |
| (b) mixture of glycerol mono- and distearate marketed under the trademark "Cerasynth SD" by ISP | | 2 % |
| (c) cetyl alcohol | | 1.5 % |
| (d) polydimethylsiloxanes marketed under the trademark "DC 200 Fluid" by Dow Corning | | 1.5 % |
| (e) benzoate of $C_{12}/C_{15}$ alcohols, marketed under the trademark "Finsolve TN" by Finetex | | 15 % |
| (f) ethylenediaminetetraacetic acid disodium salt, 2 $H_2O$ | | 0.1 % |
| (g) glycerin | | 20 % |
| (h) stabilizers | q.s. | |
| (i) demineralized water | q.s. | 100 % |

The emulsion A (comparative) additionally included a 1,3,5-triazine compound which was 2,4,6-tris[p-(2'-ethylhexyl)-1'oxycarbonyl)anilino]-1,3,5-triazine (Uvinul T 150). Emulsion B, also comparative, contained Uvinul T 150 in combination with 4-tert-butyl-4'-methoxydibenzoyl-methane (Parsol 1789). Emulsion C, according to the invention, included, besides Uvinul T 150 and Parsol 1789, 2-ethylhexyl α-cyano-β,β'-diphenylacrylate (Uvinul N 539). Emulsion D, comparative, contained Uvinul T 150 in combination with Parsol 1789, but with a conventional UV-B screening agent which was octyl methoxycinnamate (Parsol MCX).

The compositions of the emulsions A, B, C and D with regard to the various screening agents indicated above which they contained, are reported in Table I below (the quantities are expressed as weight % relative to the total weight of the composition):

TABLE I

| Screening agent | Emulsion A (comparative) | Emulsion B (comparative) | Emulsion C (invention) | Emulsion D (comparative) |
|---|---|---|---|---|
| Uvinul T 150 | 1.5% | 1.5% | 1.5% | 1.5% |
| Parsol 1789 | — | 0.5% | 0.5% | 0.5% |
| Uvinul N 539 | — | — | 10% | — |
| Parsol MCX | — | — | — | 10% |

In the case of each of these emulsions, the percentage of residual 2,4,6-tris[p-(2'-ethylhexyl-1'-oxycarbonyl) anilino]-1,3,5-triazine was determined after irradiation with UV according to the following procedure: four control samples and four test samples were prepared in the case of each formulation. 16 mg of formulation, which was spread over an area of 2 cm×4 cm, were deposited on depolished PMMA (polymethyl methacrylate) panels rinsed beforehand with water and then dried. The panels were then irradiated (Heraeus Suntest CPS) for 4 hours in a chamber where the temperature was controlled in the region of 35°–40° C. in order to simulate a natural UV irradiation, the control panels being stored in the dark during the period of irradiation of the other panels.

The samples were next treated in the following manner: the screening agents were extracted by immersing each panel in 55 ml of isopropanol in order to dissolve the screening agents. The panels and the solvent containing the screening agents were next treated with ultrasonics for 5 minutes to ensure an efficient extraction. The solutions obtained were analyzed by high performance liquid-phase chromatography.

For each formula tested, the residual proportion of 2,4,6-tris[p-(2'-ethylhexyl-1'-oxycarbonyl) anilino]-1,3,5-triazine after irradiation was determined by the ratio of its concentration in the irradiated sample to its concentration in the unirradiated sample.

The results, as percentage of remaining 2,4,6-tris[p-(2'-ethylhexyl-1'-oxycarbonyl) anilino]-1,3,5-triazine, are reported in the following Table TABLE (II):

TABLE II

| Emulsion | Residual Uvinul T 150 |
|---|---|
| Emulsion A (comparative) | 80% |
| Emulsion B (comparative) | 68% |
| Emulsion C (invention) | 99% |
| Emulsion D (comparative) | 79% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photostable, topically applicable cosmetic/dermatological sunscreen composition suited for the UV-photoprotection of human skin and/or hair, comprising (i) a UV-A photoprotecting effective amount of 4-tert-butyl-4'-methoxydibenzoylmethane, (ii) a UV-B photoprotecting effective amount of at least one 1,3,5-triazine compound having the following structural formula (I):

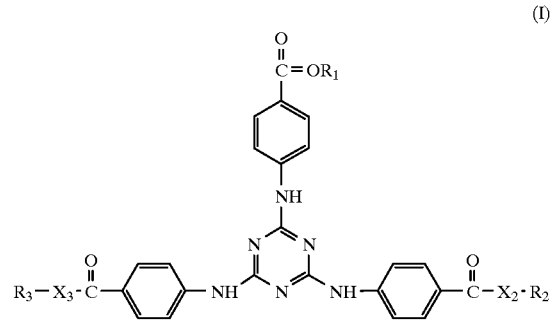

wherein $X_2$ and $X_3$, which may be identical or different, are each an oxygen atom or the -NH- radical; and $R_1$, $R_2$ and $R_3$, which may be identical or different, are each a hydrogen atom, an alkali metal, an ammonium radical optionally substituted by one or more alkyl or hydroxyalkyl radicals, a linear or branched $C_1$-$C_{18}$ alkyl radical, a $C_5$-$C_{12}$ cycloalkyl radical optionally substituted by one or more $C_1$-$C_4$ alkyl radicals, a polyoxyethylenated radical having from 1 to 6 ethylene oxide units and in which the terminal OH group is methylated, or a radical of the following formulae (II), (III) and (IV):

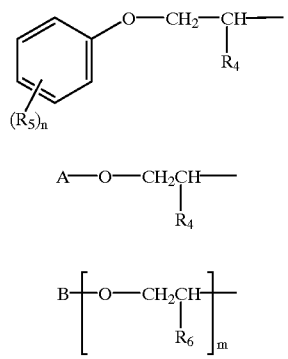

wherein R<sub>4</sub> is hydrogen or a methyl radical, $R_5$ is a $C_1$-$C_9$ alkyl radical, n is an integer ranging from 0 to 3, m is an integer ranging from 1 to 10, A is a $C_4$-$C_8$ alkyl radical or a $C_5$-$C_8$ cycloalkyl radical, B is a linear or branched $C_1$-$C_8$ alkyl radical, a $C_5$-$C_8$ cycloalkyl radical, or an aryl radical optionally substituted by one or more $C_1$-$C_4$ alkyl radicals, and $R_6$ is hydrogen or a methyl radical, and (iii) a photostabilizing effective amount of at least one alkyl β,β'-diphenylacrylate or alkyl α-cyano-β,β'-diphenylacrylate having the following structural formula (V):

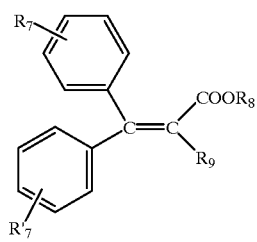

in which $R_7$ and $R'_7$, which may be identical or different, are in a meta- or para- position and are each a hydrogen atom, a straight or branched chain $C_1$-$C_8$ alkoxy radical, or a straight or branched chain $C_1$-$C_4$ alkyl radical; $R_8$ is a straight or branched chain $C_1$-$C_{12}$ alkyl radical; and $R_9$ is a hydrogen atom or a -CN radical, with the proviso that said composition is devoid of destabilizing amounts of 2-ethylhexyl p-methoxycinnamate.

2. The cosmetic/dermatological sunscreen composition as defined by claim 1, formulated in a topically applicable, cosmetically/dermatologically acceptable vehicle, diluent or carrier therefor.

3. The cosmetic/dermatological sunscreen composition as defined by claim 1, wherein said at least one 1,3,5-triazine compound having formula (I), $X_2$ and $X_3$ are identical and are each an oxygen atom, $R_1$ is a $C_5$-$C_{12}$ cycloalkyl radical optionally substituted by one or more $C_1$-$C_4$ alkyl radicals, or a radical of formula (II, (III) or (IV) in which B is a $C_1$-$C_4$ alkyl radical, and $R_6$ is the methyl radical, $R_2$ and $R_3$, which may be identical or different, are each hydrogen, an alkali metal, an ammonium radical optionally substituted by one or more alkyl or hydroxyalkyl radicals, a linear or branched $C_1$-$C_{18}$ alkyl radical, a $C_5$-$C_{12}$ cycloalkyl radical optionally substituted by one or more $C_1$-$C_4$ alkyl radicals, or a radical of formula (II), (III) or (IV) in which B is a $C_1$-$C_4$ alkyl radical, and $R_6$ is the methyl radical.

4. The cosmetic/dermatological sunscreen composition as defined by claim 1, wherein said at least one 1,3,5-triazine compound having formula (I), $X_3$ is the -NH- radical, $R_3$ is a linear or branched $C_1$-$C_{18}$ alkyl radical, or a $C_5$-$C_{12}$ cycloalkyl radical optionally substituted by one or more $C_1$-$C_4$ alkyl radicals, and $R_1$ is hydrogen, an alkali metal, an ammonium radical, a radical of formula (IV), a linear or branched $C_1$-$C_{18}$ alkyl radical or a $C_5$-$C_{12}$ cycloalkyl radical optionally substituted by one or more $C_1$-$C_4$ alkyl radicals, with the provisos that if $X_2$ is the -NH- radical, then $R_2$ is a linear or branched $C_1$-$C_{18}$ alkyl radical or a $C_5$-$C_{12}$ cycloalkyl radical optionally substituted by one or more $C_1$-$C_4$ alkyl radicals, and if $X_2$ is oxygen, then $R_2$ is hydrogen, an alkali metal, an ammonium radical, a radical of formula (IV), a linear or branched $C_1$-$C_{18}$ alkyl radical or a $C_5$-$C_{12}$ cycloalkyl radical optionally substituted by one or more $C_1$-$C_4$ alkyl radicals.

5. The cosmetic/dermatological sunscreen composition as defined by claim 1, said at least one 1,3,5-triazine compound having the following structural formula:

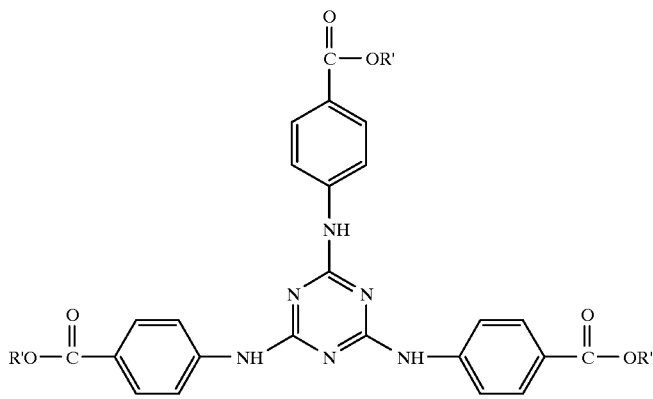

in which R' is a 2-ethylhexyl radical.

6. The cosmetic/dermatological sunscreen composition as defined by claim 1, wherein said at least one 1,3,5-triazine compound having formula (I), $X_2$ and $X_3$ are identical and are each an oxygen atom, and $R_1$, $R_2$ and $R_3$ are identical and are each a $C_6$-$C_{12}$ alkyl radical or a polyoxyethylene radical having from 1 to 6 ethylene oxide units and in which the terminal OH group is methylated.

7. The cosmetic/dermatological sunscreen composition as defined by claim 1, said at least one 1,3,5-triazine compound having the following structural formula:

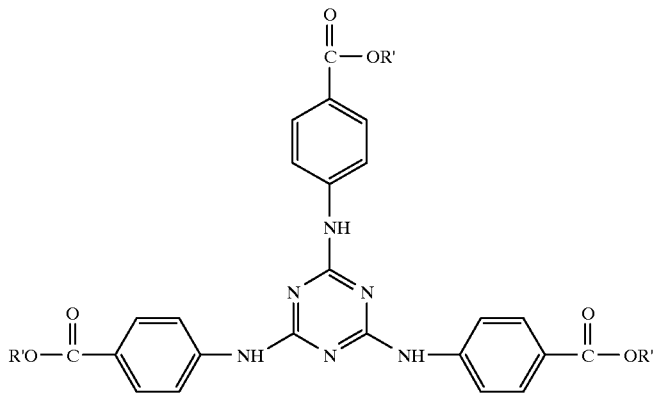

in which R' is a 2-ethylhexyl radical.

8. The cosmetic/dermatological sunscreen composition as defined by claim 1, said at least one 1,3,5-triazine compound comprising from 0.5% to 20% by weight thereof.

9. The cosmetic/dermatological sunscreen composition as defined by claim 8, said at least one 1,3,5-triazine compound comprising from 1% to 10% by weight thereof.

10. The cosmetic/dermatological sunscreen composition as defined by claim 1, said at least one alkyl β,β-diphenylacrylate or alkyl α-cyano-β,β-diphenylacrylate comprising 2-ethylhexyl α-cyano-β,β'-diphenylacrylate or ethyl α-cyano-β,β'-diphenylacrylate.

11. The cosmetic/dermatological sunscreen composition as defined by claim 1, said at least one alkyl β,β'-diphenylacrylate or alkyl α-cyano-β,β'-diphenylacrylate comprising at least 0.5% by weight thereof.

12. The cosmetic/dermatological sunscreen composition as defined by claim 11, said at least one alkyl β,β'-diphenylacrylate or alkyl α-cyano-β,β'-diphenylacrylate comprising from 0.5% to 20% by weight thereof.

13. The cosmetic/dermatological sunscreen composition as defined by claim 1, said 4-tert-butyl-4'-methoxydibenzoylmethane comprising from 0.2% to 15% by weight thereof.

14. The cosmetic/dermatological sunscreen composition as defined by claim 13, said 4-tert-butyl-4'-methoxydibenzoylmethane comprising from 0.5% to 10% by weight thereof.

15. The cosmetic/dermatological sunscreen composition as defined by claim 1, comprising an oil-in-water emulsion.

16. The cosmetic/dermatological sunscreen composition as defined by claim 1, comprising a cream, gel, milk, cream gel, stick, powder, ointment, foam, mousse or spray.

17. The cosmetic/dermatological sunscreen composition as defined by claim 1, comprising a makeup.

18. The cosmetic/dermatological sunscreen composition as defined by claim 1, further comprising at least one other UV-A and/or UV-B screening agent.

19. The cosmetic/dermatological sunscreen composition as defined by claim 1, further comprising at least one fat, organic solvent, ionic or nonionic thickening agent, softener, antioxidant, anti-free radical agent, opacifying agent, stabilizing agent, emollient, silicone, α-hydroxyacid, anti-foaming agent, hydrating agent, vitamin, fragrance, preservative, surfactant, filler, sequestering agent, polymer, propellant, basifying or acidifying agent, dye, colorant, or mixture thereof.

20. A regime for protecting human skin and/or hair against the deleterious effects of ultraviolet irradiation, comprising topically applying thereto an effective amount of the cosmetic/dermatological sunscreen composition as defined by claim 1.

21. A regime for protecting human skin and/or hair against the deleterious effects of solar radiation, comprising topically applying thereto an effective amount of the cosmetic/dermatological sunscreen composition as defined by claim 1.

* * * * *